United States Patent [19]

Higashio et al.

[11] Patent Number: 5,362,870
[45] Date of Patent: Nov. 8, 1994

[54] PROCESS FOR PRODUCING A HIGH PURITY CAPROLACTAM

[75] Inventors: Yasuhiko Higashio, Toyonaka; Hiroshi Kajikuri; Keisuke Sugita, both of Ibaraki; Hideki Doi; Masanobu Matsubara, both of Niihama, all of Japan

[73] Assignee: Sumitomo Chemical Company, Ltd., Osaka, Japan

[21] Appl. No.: 46,146

[22] Filed: Apr. 15, 1993

[30] Foreign Application Priority Data

Apr. 17, 1992 [JP] Japan ................... 4-097717
Apr. 20, 1992 [JP] Japan ................... 4-099380
Jun. 18, 1992 [JP] Japan ................... 4-159277

[51] Int. Cl.$^5$ ................................. C07D 201/16
[52] U.S. Cl. .......................... 540/540; 540/535; 540/536
[58] Field of Search ................. 540/540, 535, 536

[56] References Cited

U.S. PATENT DOCUMENTS

| | | | |
|---|---|---|---|
| 3,755,305 | 8/1973 | Schwarz et al. | 540/540 |
| 3,794,647 | 2/1974 | Henn et al. | 540/540 |
| 3,966,712 | 6/1976 | Immel et al. | 540/540 |
| 4,148,792 | 4/1979 | Danziger et al. | 540/540 |
| 4,610,768 | 9/1986 | Moosavian | 540/540 |

FOREIGN PATENT DOCUMENTS

| | | | |
|---|---|---|---|
| 2023344 | 11/1971 | Germany | 540/540 |
| 2109431 | 11/1971 | Germany | 540/540 |
| 2148717 | 4/1972 | Germany | 540/540 |
| 2153312 | 4/1972 | Germany | 540/540 |
| 2163258 | 6/1972 | Germany | 540/540 |
| 2163259 | 9/1972 | Germany | 540/540 |
| 2203945 | 8/1973 | Germany | 540/540 |
| 2641449 | 3/1978 | Germany | 540/540 |
| 2641478 | 3/1978 | Germany | 540/540 |
| 763954 | 12/1956 | United Kingdom | 540/540 |

*Primary Examiner*—Robert T. Bond
*Attorney, Agent, or Firm*—Cushman, Darby & Cushman

[57] ABSTRACT

A process for producing a high purity caprolactam is disclosed in which a crude caprolactam obtained by a catalytic rearrangement of cyclohexanone oxime is subjected (1) to mixing, while stirring, with at least one hydrocarbon selected from the group consisting of aliphatic hydrocarbons and alicyclic hydrocarbons to form a liquid-liquid, two-layer liquid mixture, and then crystallizing caprolactam out of the liquid mixture;

(2) to mixing with both at least one hydrocarbon selected from the group consisting of aliphatic hydrocarbons and alicyclic hydrocarbons, and water to form a liquid mixture, separating the liquid mixture into a hydrocarbon layer and a water layer, and then recovering caprolactam from the water layer; or (3) to distillation in the co-presence of at least one aliphatic saturated hydrocarbon of 10 to 18 carbon atoms.

5 Claims, No Drawings

PROCESS FOR PRODUCING A HIGH PURITY CAPROLACTAM

The present invention relates to a process for producing caprolactam. More particularly, the present invention relates to a process for producing a high purity caprolactam which comprises subjecting a crude caprolactam obtained by a catalytic rearrangement of cyclohexanone oxime (1) to mixing, while stirring, with at least one hydrocarbon selected from the group consisting of aliphatic hydrocarbons and alicyclic hydrocarbons to form a liquid-liquid, two-layer liquid mixture, and then crystallizing caprolactam out of the liquid mixture;

(2) to mixing with both at least one hydrocarbon selected from the group consisting of aliphatic hydrocarbons and alicyclic hydrocarbons, and water to form a liquid mixture, separating the liquid mixture into a hydrocarbon layer and a water layer, and then recovering caprolactam from the water layer; or (3) to distillation in the co-presence of at least one aliphatic saturated hydrocarbon of 10 to 18 carbon atoms.

A caprolactam of high purity has been used as a raw material for polyamide fibers and polyamide resins. The caprolactam for the raw material is well known to be produced by subjecting cyclohexanone oxime to rearrangement in a sulfuric acid medium to form caprolactam, neutralizing it with an aqueous ammonia, extracting the caprolactam with an aromatic solvent such as benzene, separating the solvent from the caprolactam by distillation to obtain a crude caprolactam, and then purifying the crude caprolactam by subjecting it to precision fractionation ("Kogyo Yuki Kagaku (Industrial Organic Chemistry)", page 244, (1989, Tokyo Kagaku Dojin)).

However, a problem arose that caprolactam can not be extracted in a layer of an aromatic solvent such as benzene when cyclohexanone oxime is subjected to a catalytic rearrangement by using a solid catalyst instead of sulfuric acid, even if a crude caprolactam was dissolved in water in advance and then mixed with the aromatic solvent, possibly due to the fact that the aqueous solution does not contain an inorganic material. Thus, the method mentioned above in which cyclohexanone oxime is rearranged in a sulfuric acid medium can not be applied.

Moreover, another problem arose that a caprolactam of satisfiable quality can not be obtained even when a crude caprolactam obtained by a catalytic rearrangement was subjected to precision fractionation, perhaps because by-products are different from those formed in the rearrangement in a sulfuric acid medium. Particularly, octahydrophenazine which gives an adverse effect to a quality standard, UV value of caprolactam can hardly be removed through distillation.

On the other hand, in order to produce a caprolactam of high quality through a catalytic rearrangement of cyclohexanone oxime, there are proposed a method in which a crude caprolactam obtained through a catalytic rearrangement is reacted with potassium permanganate, dissolved in toluene, and then crystallized out of toluene (Japanese Patent Kokai No. Sho 53-37687) and another method in which a crude caprolactam is dissolved in a polar solvent such as dimethyl formamide and then crystallized therefrom (Japanese Patent Kokai No. Sho 49-54389). However, the methods are not entirely satisfactory because they have problems that complex apparatuses are required to use, operation is intricate, and the recovery percentage of caprolactam is low.

Further, a method for producing a caprolactam of high purity is known in which a liquid-liquid, two-layer liquid mixture comprising a crude caprolactam and an aliphatic hydrocarbon such as isooctane is prepared, a layer of the caprolactam in which by-products are concentrated is separated from the hydrocarbon layer to remove the impurities, and then caprolactam is crystallized out of the hydrocarbon layer (Japanese Patent Kokai No. Sho 46-5231). However, since the caprolactam layer is removed, this method has problems not only that the yield of caprolactam is low and operation is complicated, but also that a large quantity of a solvent of 3 to 6 times by weight as much as the crude caprolactam is required.

During the course of investigation by the present inventors for developing an excellent process for producing a caprolactam of high purity through a catalytic rearrangement of cyclohexanone oxime, it has been found that a high purity caprolactam can be prepared by subjecting a crude caprolactam which is obtained by a catalytic rearrangement to crystallization, extraction, or distillation, leading to further study to establish the process of the present invention.

That is, the present invention is to provide a process for producing a high purity caprolactam which comprises subjecting a crude caprolactam obtained by a catalytic rearrangement of cyclohexane oxime (1) to mixing, while stirring, with at least one hydrocarbon selected from the group consisting of aliphatic hydrocarbons and alicyclic hydrocarbons to form a liquid-liquid, two-layer liquid mixture, and then crystallizing caprolactam out of the liquid mixture;

(2) to mixing with both at least one hydrocarbon selected from the group consisting of aliphatic hydrocarbons and alicyclic hydrocarbons, and water to form a liquid mixture, separating the liquid mixture into a hydrocarbon layer and a water layer, and then recovering caprolactam from the water layer; or (3) to distillation in the co-presence of at least one aliphatic saturated hydrocarbon of 10 to 18 carbon atoms.

The present invention will now be described in detail with reference to embodiments.

In the present invention, cyclohexanone oxime is subjected to a catalytic rearrangement to form a crude caprolactam and then purified. The catalytic rearrangement is carried out by using a solid catalyst, for example, a boric acid catalyst (Japanese Patent Kokai No. Sho 53-37686), a silica-alumina catalyst (British Patent No. 831,927), a solid phosphoric acid catalyst (British Patent No. 881,926), and a zeolite catalyst (Japanese Patent Kokai No. Sho 62-123167). The present invention is particularly efficient when the catalytic rearrangement is performed in a gas phase.

A crude caprolactam obtained by a catalytic rearrangement is preferably subjected to a purification after by-products having a high boiling point and an additive when it is added to the reaction system are separated by distillation or by another method, while the crude caprolactam may be subjected to purification as it is in the state of reaction liquid after the catalytic rearrangement.

Next, each of the procedures (1) to (3) mentioned above will be explained in more specifically.

First, the conditions in the procedure (1) are explained in which a crude caprolactam obtained through a catalytic rearrangement of cyclohexanone oxime is mixed, while being stirred, with at least one hydrocarbon selected from the group consisting of aliphatic hydrocarbons and alicyclic hydrocarbons to form a liquid-liquid, two-layer liquid mixture, and then caprolactam is crystallized out of the liquid mixture.

The aliphatic hydrocarbon and alicyclic hydrocarbon to be used in this procedure include hydrocarbons of 6 to 12 carbon atoms, such as cyclohexane, n-heptane, isoctane, and n-decane. Two or more of the hydrocarbons may be used in combination. The boiling point of the hydrocarbons is preferably higher than the melting point of a crude caprolactam, and in this case, the process of the procedure (1) can be conducted under an atmospheric pressure.

The amount of the hydrocarbon to be used may be such that the hydrocarbon and caprolactam form a heterogeneous, liquid-liquid layer at a temperature higher than the melting point of caprolactam, and it is usually 0.05 to 2 times by weight, preferably 0.1 to 1 time by weight as much as caprolactam.

In the practice of the procedure (1), for instance, a crude caprolactam is mixed with the hydrocarbon mentioned above under a heated condition to form a heterogeneous liquid-liquid, two-layer liquid mixture and caprolactam is crystallized out of the liquid mixture by cooling the liquid mixture while stirring. In this step, almost all impurities contained in the crude caprolactam is extracted in a hydrocarbon layer.

Then, the crystals are separated by a conventional means such as filtration, washed with the hydrocarbon, if necessary, and finally dried to obtain a caprolactam of high purity containing no impurities such as octahydrophenazine. This caprolactam may further be purified by a purification means such as distillation under a reduced pressure to obtain a caprolactam of higher purity.

According to the procedure (1), a high quality caprolactam can easily be produced at a high yield through quite a simple operation in which caprolactam is crystallized out of a liquid-liquid, two-layer liquid mixture comprising a crude caprolactam and a hydrocarbon.

In addition, the procedure (1) is advantageous to the production of a high purity caprolactam in a commercial scale since the amount of the solvent to be used can be largely reduced, the apparatuses to be utilized can be miniaturized, and the energy to be consumed can be saved.

Next, the conditions in the procedure (2) mentioned above are explained in which a crude caprolactam is mixed with both at least one hydrocarbon selected from the group consisting of aliphatic hydrocarbons and alicyclic hydrocarbons, and water to form a liquid mixture, the liquid mixture is separated into a hydrocarbon layer and a water layer, and then caprolactam is recovered from the water layer.

The aliphatic hydrocarbon and alicyclic hydrocarbon to be used in the procedure (2) include hydrocarbons of 5 to 15 carbon atoms, such as n-pentane, n-hexane, cyclohexane, n-heptane, methyl cyclohexane, isoctane, n-decane, dodecane, and pentadecane. Two or more of the hydrocarbons may be used in combination.

The hydrocarbon is used usually in an amount of 0.2 to 5 times by weight, preferably in an amount of 0.5 to 2 times by weight as much as the crude caprolactam.

The water is used usually in an amount of 0.2 to 5 times by weight, preferably in an amount of 0.5 to 2 time by weight as much as the crude caprolactam.

In the practice of the procedure (2), a crude caprolactam is mixed with both the hydrocarbon and water. At this step, almost all caprolactam is extracted in a water layer, and almost all impurities contained in the crude caprolactam are extracted in a hydrocarbon layer.

After the separation of the liquid mixture into two layers, water is separated from the water layer containing caprolactam thereby a caprolactam of high purity containing no octahydrophenazine and other impurities can be obtained. When the water is separated after the separated water layer was subjected to extraction of impurities with the hydrocarbon mentioned above, a caprolactam of higher purity can be obtained. As a method for separating water, a method for distilling off water is usually adopted.

As a method for the extraction, a method which is called "multistage extracting operation" may be used.

While a caprolactam of high quality can be obtained according to the steps mentioned above, the caprolactam may further be purified by subjecting it to a purification means such as distillation under a reduced pressure to obtain a caprolactam of higher purity.

According to the procedure (2), a caprolactam of high quality can easily be produced at a high yield by mixing a crude caprolactam with a hydrocarbon and water to form a liquid mixture, separating the liquid mixture into a hydrocarbon layer and a water layer, and then recovering caprolactam from the water layer.

Next, the conditions in the procedure (3) mentioned above are explained in which a crude caprolactam is distilled in the co-presence of an aliphatic saturated hydrocarbon of 10 to 18 carbon atoms.

The aliphatic saturated hydrocarbon to be used in the procedure (3) includes aliphatic hydrocarbons of 10 to 18 carbon atoms such as decane, undecane, dodecane, tridecane, tetradecane, pentadecane, hexadecane, heptadecane, and octadecane. Among the hydrocarbons, tetradecane, pentadecane, and hexadecane are preferably used.

The hydrocarbon is used usually in an amount of 0.5 to 20 times by weight, preferably in an amount of 2 to 10 times by weight as much as the crude caprolactam.

In the distillation, a crude caprolactam and hydrocarbon may be premixed and then supplied to a distillation system. Alternatively, they may be separately introduced into a distillation system. Distillation may be either batch and continuous type.

While the pressure and temperature at the distillation depend on particular hydrocarbon to be used, the pressure is usually 2 to 500 mmHg at the top of a distillation column and the temperature is usually 80 to 200° C. at the top of a distillation column.

Caprolactam and the hydrocarbon are distilled off as an azeotropic mixture from the top of a distillation column. The distillate is subjected to separation and then caprolactam and hydrocarbon are separated from each other to recover by a means such as distillation. Recovered hydrocarbon may be used repeatedly.

While a high purity caprolactam containing no impurities such as octahydrophenazine can be obtained through the procedure (3) mentioned above, the caprolactam may further be purified by a purification means such as a distillation under a reduced pressure to obtain a caprolactam of higher purity.

According to the procedure (3), a caprolactam of high quality can easily be produced efficiently by distilling a crude caprolactam in the co-presence of at least one aliphatic saturated hydrocarbon.

EXAMPLE

Now, the present invention will be described in further detail in reference to Examples. However, it should be understood that the present invention is by no means restricted by such specific Examples.

Example 1

A crude caprolactam (caprolactam: 94.2%, octahydrophenazine: 1200 ppm) was obtained by a catalytic rearrangement of cyclohexanone oxime by using a zeolite catalyst.

In a flask equipped with a stirrer were charged 60 g of the crude caprolactam and 30 g of isooctane, and heated up to 80° C. under stirring.

When stirring was stopped, the liquid mixture was separated into two layers, the layer (lower layer) of melted caprolactam and the layer (upper layer) of isooctane.

While rotating the stirrer at a speed of 400 rpm, the liquid mixture was gradually cooled down to 25° C. to precipitate crystals, and subjected to filtration and drying to obtain 57 g of caprolactam.

The crystals were analyzed by gas chromatography to obtain the results that the purity of the crystals was 99.6% and the content of octahydrophenazine was less than a detection limit.

In this Example, deposition of crystals on the wall surface of the flask or to the stirrer was not observed, and the crystals were granular crystals of a uniform diameter and easy to filtrate.

Examples 2 to 3 and Comparative Example 1

Example 1 was repeated except that one of the solvents as shown in Table 1 was used instead of isooctane. The results are shown in Table 1.

In all of these Examples and Comparative Example, the content of octahydrophenazine was less than a detection limit.

TABLE 1

| Example | Solvent | Status (80° C.) | Caprolactam Amount of recovery | Purity (%) |
|---|---|---|---|---|
| Example 2 | Cyclohexane | Liquid-liquid, two-layer heterogeneous | 53 | 99.4 |
| Example 3 | n-decane | Liquid-liquid, two-layer heterogeneous | 54 | 99.3 |
| Comparative Example 1 | Toluene | Homogeneous | 32 | 99.5 |

Comparative Example 2

Example 1 was repeated except that the amount of isooctane was increased to 300 g to obtain 38 g of caprolactam. The purity of the crystals obtained was 99.5% and the content of octahydrophenazine was less than a detection limit.

In this Comparative Example, all of caprolactam was dissolved in isooctane to form a homogeneous solution at the time when the temperature was raised to 80° C. Deposition of crystals on the wall surface of the flask was observed after the crystallization, the crystals obtained were plate crystals in irregular shape, and a long period of time was required for filtration of the crystals.

Comparative Example 3

The same crude caprolactam as used in Example 1 in an amount of 50 g was subjected to fractional distillation using a distillation column (number of actual stages: 20) under a pressure of 5 mmHg at a reflux ratio of 5 to obtain 32 g of caprolactam fraction. The caprolactam had a purity of 99.7% and contained 800 ppm of octahydrophenazine.

Referential Example 1

Comparative Example 3 was repeated except that the caprolactam obtained in Example 1 was used instead of the crude caprolactam to obtain 36 g of caprolactam fraction.

The purity of the caprolactam fraction thus obtained was 99.97% and the content of octahydrophenazine was less than a detection limit.

Example 4

In a flask, 60 g of the same crude caprolactam as used in Example 1, 60 g of water, and 60 g of cyclohexane were charged, stirred for 1 hour at an ambient temperature, and allowed to stand to separate.

To the water layer thus formed was charged 60 g of cyclohexane, stirred for 1 hour at the same temperature as above, and allowed to stand to separate. This operation was repeated 3 times and the water layer formed was supplied to an evaporator to distill off water and to recover 58 g of caprolactam.

The caprolactam was analyzed by gas chromatography to obtain the results that the purity of the caprolactam was 99.2% and the content of octahydrophenazine was less than a detection limit.

Examples 5 to 6 and Comparative Example 4

Example 4 was repeated except that one of the solvents shown in Table 2 was used. The results are shown in Table 2.

In all of these Examples and Comparative Example, the content of octahydrophenazine was less than a detection limit.

TABLE 2

| Example | Solvent | Caprolactam Purity | Amount of Recovery (g) | Yield (%) | Recovery Ratio |
|---|---|---|---|---|---|
| Example 4 | Cyclohexane | 99.2 | 58 | 96.7 | 3.1 |
| Example 5 | Iso-Octane | 99.1 | 57 | 95 | 3.0 |
| Example 6 | n-decane | 99.0 | 57 | 95 | 3.0 |
| Comparative Example 4 | Benzene | 99.4 | 19 | 31.7 | 1.0 |

Referential Example 2

Comparative Example 3 was repeated except that the caprolactam obtained in Example 4 was used instead of the crude caprolactam to obtain 36 g of caprolactam fraction.

The purity of the caprolactam thus obtained was 99.96% and the content of octahydrophenazine was less than a detection limit.

Example 7

In a distiller having a distillation column of 20 actual stages were charged 100 g of the same crude caprolactam as used in Example 1 and 500 g of tetradecane, and subjected to distillation under a pressure of 5 mmHg at the top of the distillation column at a reflux ratio of 5 to obtain 330 g of caprolactam fraction containing tetradecane. By subjecting the fraction to separation, 74 g of caprolactam containing about 1% of tetradecane was obtained.

The results of analysis by gas chromatography of the caprolactam thus obtained are shown in Table 3. In the Table 3, purity is shown in the values in which the amount of tetradecane is deducted.

Example 8 to 9

Example 7 was repeated except that one of the hydrocarbons shown in Table 3 was used. The results are shown also in Table 3.

TABLE 3

| | | Caprolactam | | |
|---|---|---|---|---|
| Example | Hydrocarbon | Amount of recovery (g) | Purity (%)* | Amount of octahydrophenazine |
| Example 7 | Tetradecane | 74 | 99.8 | not detected |
| Example 8 | n-decane | 70 | 99.7 | not detected |
| Example 9 | Dodecane | 73 | 99.8 | not detected |

*The purity after deduction of hydrocarbon

Referential Example 3

Comparative Example 3 was repeated except that the caprolactam obtained in Example 7 was used instead of the crude caprolactam to obtain 38 g of caprolactam fraction.

The purity of caprolactam thus obtained was 99.99 % and the octahydrophenazine was not detected.

What is claimed is:

1. A process for producing a high purity caprolactam which comprises
   forming a liquid mixture by mixing a crude caprolactam obtained by a catalytic rearrangement of cyclohexanone oxime with water and at least one hydrocarbon selected from the group consisting of aliphatic hydrocarbons and alicyclic hydrocarbons;
   separating the liquid mixture into a hydrocarbon layer and a water layer; and
   recovering the high purity caprolactam from the water layer.

2. A process for producing a high purity caprolactam which comprises subjecting a crude caprolactam obtained by a catalytic rearrangement of cyclohexanone oxime to mixing with both at least one hydrocarbon selected from the group consisting of aliphatic hydrocarbons and alicyclic hydrocarbons, and water to form a liquid mixture, separating the liquid mixture into a hydrocarbon layer and a water layer, and then recovering caprolactam from the water layer.

3. The process according to claim 1, wherein the hydrocarbon has 5 to 15 carbon atoms.

4. The process according to claim 1, wherein water is used in amount of 0.2 to 5 times by weight as much as the crude caprolactam.

5. The process according to claim 1, wherein the hydrocarbon is used in an amount of 0.2 to 5 times by weight as much as the crude caprolactam.

* * * * *